United States Patent
Ojo-Amaize et al.

(10) Patent No.: US 6,242,484 B1
(45) Date of Patent: Jun. 5, 2001

(54) HYPOESTOXIDES, DERIVATIVES AND AGONISTS THEREOF FOR USE OF ANTIPARASITIC AGENTS

(75) Inventors: Emmanuel A. Ojo-Amaize, Glendora, CA (US); Joseph I. Okogun, New Rochelle, NY (US); Emeka J. Nchekwube, Morgan Hill, CA (US)

(73) Assignee: Paraquest, Inc., Bloomington, CA (US)

( * ) Notice: Subject to any disclaimer, the term of this patent is extended or adjusted under 35 U.S.C. 154(b) by 0 days.

(21) Appl. No.: 09/347,900

(22) Filed: Jul. 6, 1999

(51) Int. Cl.$^7$ .................. A61K 31/27; A61K 31/535; A01N 43/20; A01N 43/24; C07D 413/00
(52) U.S. Cl. ............... 514/475; 514/232.8; 544/147; 549/551
(58) Field of Search ................ 514/475, 232.8; 544/147; 549/551

(56) References Cited

U.S. PATENT DOCUMENTS 5,801,193 * 9/1998 Ojo-Amaize ................ 514/475

OTHER PUBLICATIONS

WHO. World malaria situation in 1994. Wkly Epidemiol Rec. 1997; 72 269–76.
Walsh, J.A. Disease problems in the Third World. Annals of the New York Academy of Sciences 1989; 569:1–16.
Oaks, S.C; Mitchell, V.S.; Pearson, G.W. and Carpenter, C.C.J; eds,. 1991. Malaria: Obstacles and Opportunities. Washington D C.: National Academy Press.
Olliaro, P., Cattani J and Wirth, D. Malaria, the submerged disease. JAMA 1996; 275: 230–233.
Bogitsh, B.J. and Chen, T.C, eds. Human Parasitology 2nd edition, 1998: Academic Press, San Diego, London, Boston, New York.
Miller, L.H; Pino J.A, McKelvey, Jr., J.J. eds. Immunity to blood parasites of animals and man. (Advances in experimental Medicine and Biology vol. 93), 1997: Plenum Press, New York and London.
Baker, J.R.; Muller, R, and Rollinson, D. eds. Advances in Parasitology vol. 43, 1999: Academic Press.
Murray, P.K. et al. eds. Medical Microbiology. Third edition, Mosby, St. Louis, MO. 1998.
Ojo–Amaize, E.A. et al. Plasmodium berghei sporozoites are mitogenic for murine T cells, induce interferon and activate natural killer cells. J. Immunol 1984, 133: 1005–1009.
Ojo–Amaize, E.A. et al. Positive correlation between degree of parasitemia, interferon titers, and natural killer cell activity in Plasmodium falciparum–infected children. J. Immunol. 1981, 127:2296–2300.
Okogun, J. I. et al. Roseanolone: A new diterpene from Hypoestes rosea. Z. Naturforsch 37c:558–561. 1982.
Adesomoju, A. A. et al. Roseadione, a diterpene Ketone from hypoestes rosea. Phytochemistry vol. 22, No. 11:2535–2536, 1983.

* cited by examiner

*Primary Examiner*—Theodore J. Criares
(74) *Attorney, Agent, or Firm*—Pillsbury Winthrop LLP

(57) ABSTRACT

Novel enhanced usage of hypoestoxides derivatives and agonists theeof as active agents against nucleated infectious entities including known parasites and the like microbiological insultors of living tissue, systems and organisms, known modes of administration and related compounds are used alone or in combination with the instant teachings.

14 Claims, 3 Drawing Sheets

HYPOESTOXIDES, DERIVATIVES AND AGONISTS THEREOF FOR USE OF ANTIPARASITIC AGENTS

BACKGROUND OF THE INVENTION

1. Cross Reference to Related Applications

Expressly incorporated herein by reference are U.S. Pat. No. 5,801,193, and co-pending applications, U.S. Ser. Nos. 09/006,946; 09/007,308; 09/298,653; and PCT WO 98/46222.

2. Field of the Invention

This invention relates to the use of diterpene compounds, in particular hypoestoxides, derivatives and agonists thereof for anti-parasitic therapy and prophylaxis, wherein unexpected and beneficial results have been noted against nucleated infectious agents, among other things.

3. Background Art

Almost a third of the world's population lives in areas at risk of malaria, and according to estimates by World Health Organization (WHO), one to two million children in Sub-Saharan Africa die from the disease each year (WHO, Wkly Epidemiol Rec. 1997; 72: 269–76). This long-standing problem has not been addressed by conventional disclosures and remains a pressing issue in most of the developing nations of the world, in addition to demanding instant clinical study.

Malaria is caused by the protozoan parasites *Plasmodium falciparum, P. vivax, P. ovale* and *P. malariae* in humans and by *P. berghei, P. chabaudi, P. yoelii, P. vinckei* in rodents; *P. knowlesi, P. cynomolgi* in primates and *P. lophurae* in avian. Malaria is the most deadly protozoan infection of humans. Hundreds of millions of cases of malaria occur annually and infections with *P. falciparum* the most virulent human malaria parasite, leads to millions of deaths each year (Walsh J. A. Annals of the New York Acad. Sciences 1989; 569: 1–16). Despite extensive control efforts, the incidence of malaria is not decreasing in most endemic areas of the world, and in some areas, it is clearly increasing (Oaks et al, eds. 1991: Washington, D.C.: National Academy Press). A major reason for the persistence of the severe malaria problem is the increasing resistance of parasites to available chemotherapeutic agents. Resistance to chloroquine, the most widely used antimalarial in the last 50 years, is now very common, and other available antimalarials are limited by resistance, high cost and toxicity (Olliaro et al; JMA 1996, 275:230–233).

Other antimalarials such as atrabrine dihydrochloride (quinacrine hydrochloride) produces a number of undesirable side effects, such as jaundice and gastrointestinal disturbances (Bogitsh, B. J. and Chen, T. C. eds. Human Parasitology, 2nd edition, 1998:Academic Press, San Diego, London, Boston, New York, etc.). Thus, the development of antimalarial drugs must be a continuous process, and requires both theoretical and clinical attention urgently.

SUMMARY OF THE INVENTION

To provide a solution to this longstanding need an unexpected use of the instant compounds has generated the teaching of the present invention, which overcome the drawbacks of the prior art.

Applicants' invention rests on their finding that a select group of hypoestoxide analogs possess unexpected prophylactic and therapeutic effectiveness as growth inhibiting agents against harmful organisms including the known protozoan parasite of the genus, Plasmodium, among others having similar status as nucleated infectious agents.

In particular, the present invention comprises a method for inhibiting and/or delaying the growth of these parasites in subjects. The method comprises administering to a subject in need of antiparasitic therapy or prophylaxis, a pharmaceutical composition comprising a therapeutically effective amount of a compound of the formula I.

In another aspect, the invention provides a method of treating a subject to alleviate pathological effects of the growth of parasites of numerous other members of the Protozoan family and related microorganisms (e.g Plasmodia, Trypanosoma, Theileria, Babesia and Coccidia).

According to a feature of the present invention there is provided a therapeutic method for treating a subject having a disease caused by infection with a protozoan parasite, comprising inhibiting the growth of said parasite by administering to said subject an effective amount of at least one compound, or a pharmaceutically acceptable prodrug of said compound, said compound having the structural formula I:

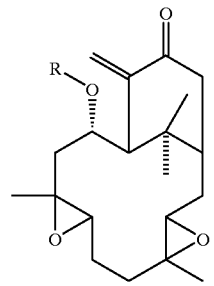

wherein R is:
a) H,
b) $P(O)(OH)_2$,
c) $P(O)(OH)(OM)$, wherein M is an alkali metal salt, or an alkaline earth metal salt,
d) $P(O)OM_2$ wherein M is each independently selected from the group consisting of alkali metal salts and alkaline earth metal salts,
e) Alkyl of 1 to 12 carbon atoms substituted or unsubstituted, straight chain or branched, 0 to 6 double bonds, $(CH_2)_n$morpholine where $n=1-4$, morpholinomethylphenyl, ortho-aminophenyl, ortho-hydroxyphenyl, $(CH_2)_nCOOR_2$ where $n=1-4$;
wherein $R_2$ is H, an alkali metal salt, an alkaline earth metal salt, $NH_4+$, $N+(R_3)_4$ wherein $R_3$ is each independently selected from the group consisting of H and alkyl of 1 to 4 carbon atoms,
f) $COR_1$ wherein $R_1$ is selected from the group consisting of H, $(CH_2)_nCH_3$ wherein $n=0-6$, $(CH_2)_nCOOR_2$ wherein $n=1-4$ and $R_2$ is as previously defined, and $(CH_2)_nN+(R_3)_3$, wherein $n=1-4$, wherein the effective amount is sufficient to ameliorate at least one symptom of said disease.

Likewise, according to a further feature of the present invention there is provided a prophylactic method for protecting a subject in danger of contracting disease caused by infection with a protozoan parasite, comprising inhibiting the growth of said parasite by administering to said subject an effective amount of at least one compound, or pharmaceutically acceptable prodrug of said compound, said compound having the structural formula I:

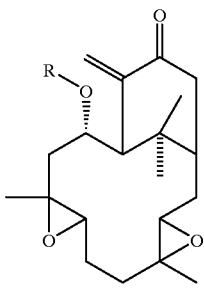

wherein R is:
 a) H,
 b) $P(O)(OH)_2$,
 c) $P(O)OH)(OM)$, wherein M is an alkali metal salt, or an alkaline earth metal salt,
 d) $P(O)OM_2$ wherein M is each independently selected from the group consisting of alkali metal salts and alkaline earth metal salts,
 e) alkyl of 1 to 12 carbon atoms substituted or unsubstituted, straight chain or branched, 0 to 6 double bonds, $(CH_2)_n$morpholine where n=1-4, morpholinomethylphenyl, ortho-aminophenyl, ortho-hydroxyphenyl, $(CH_2)_nCOOR_2$ where n=1-4;
 f) wherein $R_2$ is H, an alkali metal salt, an alkaline earth metal salt, $NH_4+$, $N+(R_3)_4$ wherein $R_3$ is each independently selected from the group consisting of H and alkyl of 1 to 4 carbon atoms,
 g) $COR_1$ wherein $R_1$ is selected from the group consisting of H, $(CH_2)_nCH_3$ wherein n=0-6, $(CH_2)_nCOOR_2$ wherein n=1-4 and $R_2$ is as previously defined, and $(CH_2)_nN+(R_3)_3$, wherein n=1-4,
 wherein the effective amount is sufficient to ameliorate the manifestation of at least one symptom of said disease.

These, and other objects, features and advantages of the present invention will become apparent when read in conjunction with the accompanying figures.

BRIEF DESCRIPTION OF THE DRAWINGS

FIG. 3 shows the actual day of death of individual mouse in each group over a 24-day period. The group of mice administered with 125 µg/kg of JO-4A survived the longest (about 3 times longer than the control group).

DETAILED DESCRIPTION OF PREFERRED EMBODIMENTS

Figure 1:
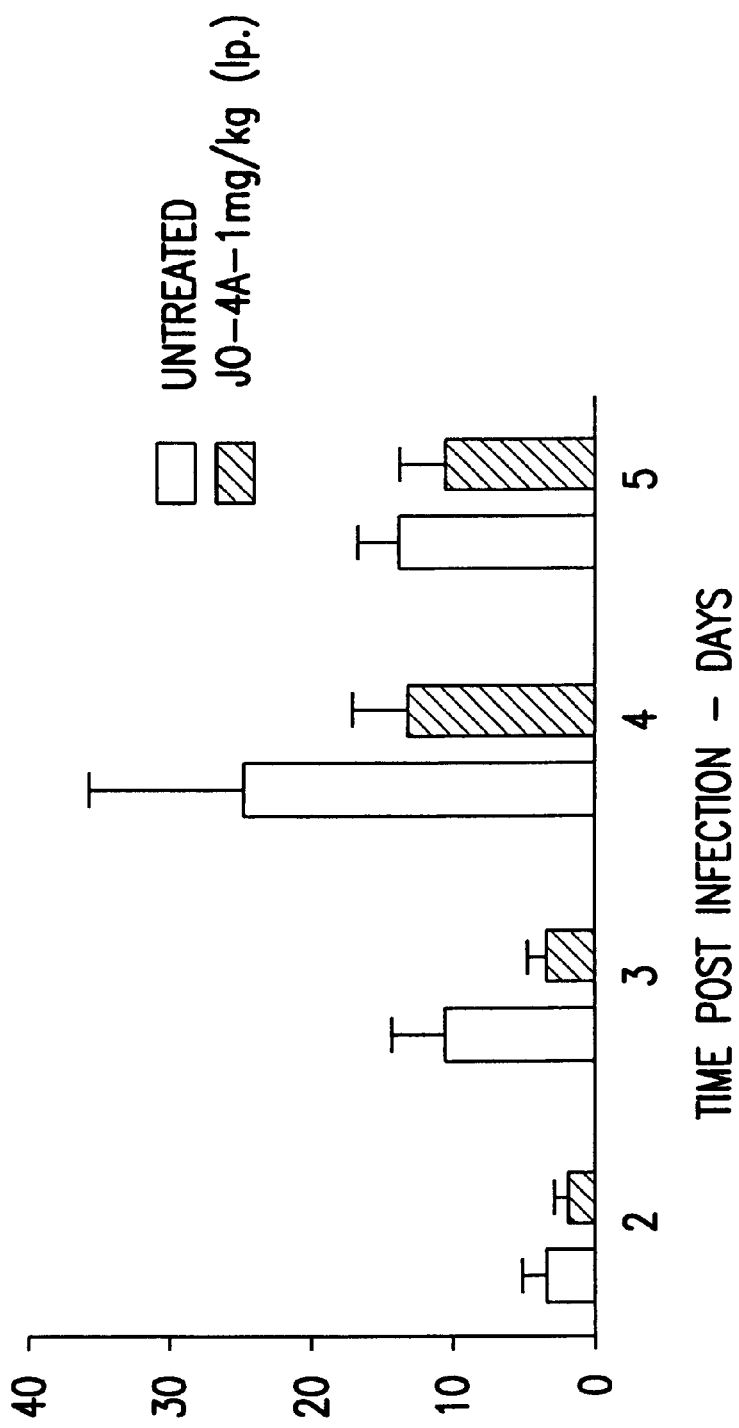
FIG. 1 shows the prophylactic effect of JO-4A on the level of parasitemia of *Plasmodium berghei* malaria parasites in the blood of mice infected with the murine parasites. C57BL/6 inbred strains of mice were pretreated intraperitoneally (i.p.) for 3 days with 1.0 mg/kg of JO-4A. On the 4th day, mice were infected with live parasites. Blood samples were obtained from the mice on days 2, 3, 4, and 5 post infection to determine the level of blood parasitemia. The results demonstrate that pretreatment of mice with JO-4A prior to infection with malaria parasites dramatically reduced the level of parasitemia in the blood in the first four days of infection.
Figure 2:
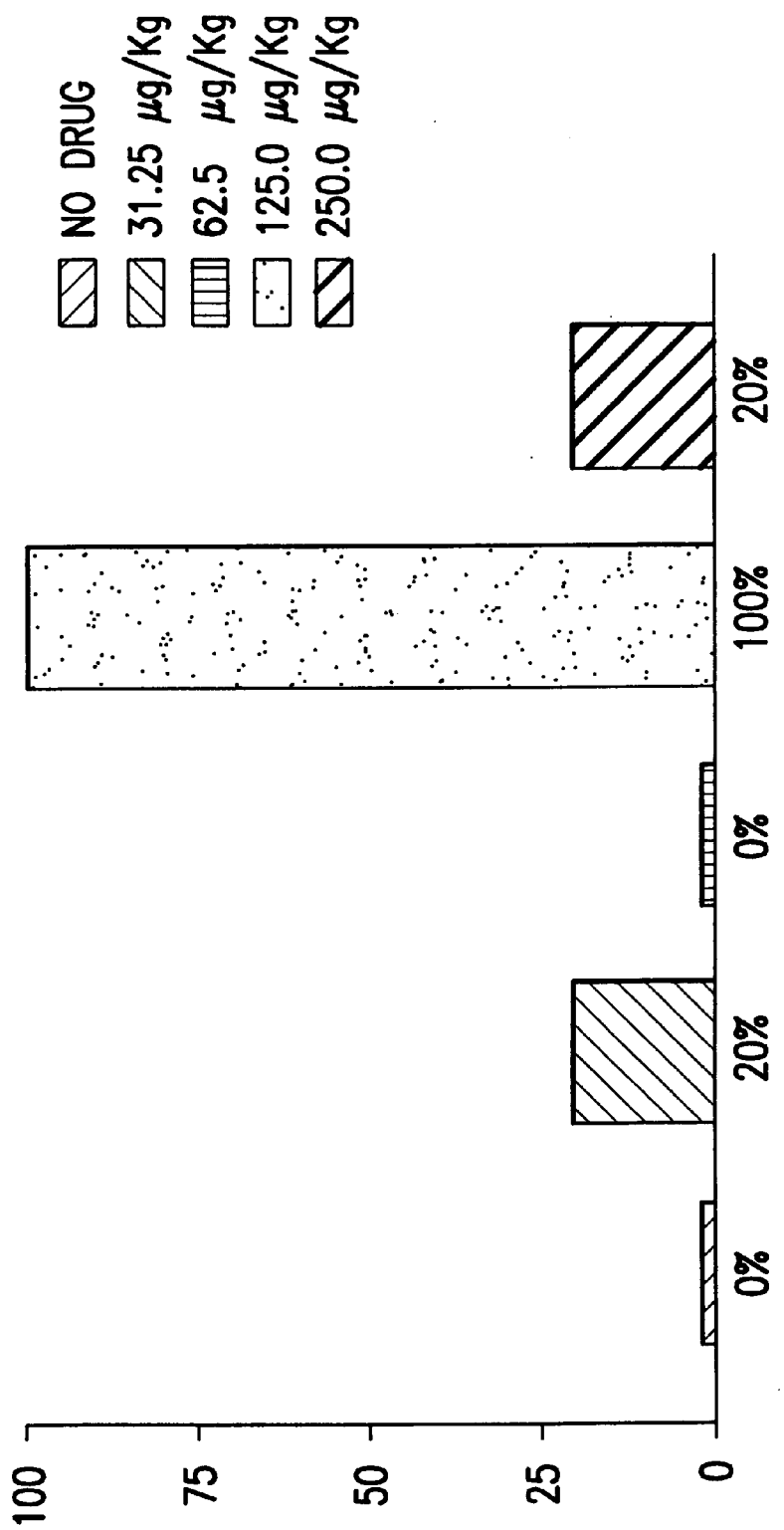
FIG. 2 shows the combined prophylactic and therapeutic effects of JO-4A on the survival of mice infected with *P. berghei* parasites, 8 days post infection. Mice in the different groups (10 mice per group) were pretreated per oral (p.o.) daily for 5 days with varying doses of JO-4A in water (31.25 µg/kg, 62.5 µg/kg, 125.0 µg/kg and 250.0 µg/kg). The control group was given water only. On the 5th day of JO-4A pretreatment; all mice were infected with *P. berghei* parasites i.p. Daily treatment with JO-4A was continued for 3 days post-infection. The results depicted in FIG. 2 were obtained 8 days post infection with *P. berghei* parasites. Whereas all mice in the control group which did not receive JO-4A, died by day 8 post infection with *P. berghei* parasites, none of the mice treated with 125.0 µg/kg of JO-4A, died by this day.
Figure 3:
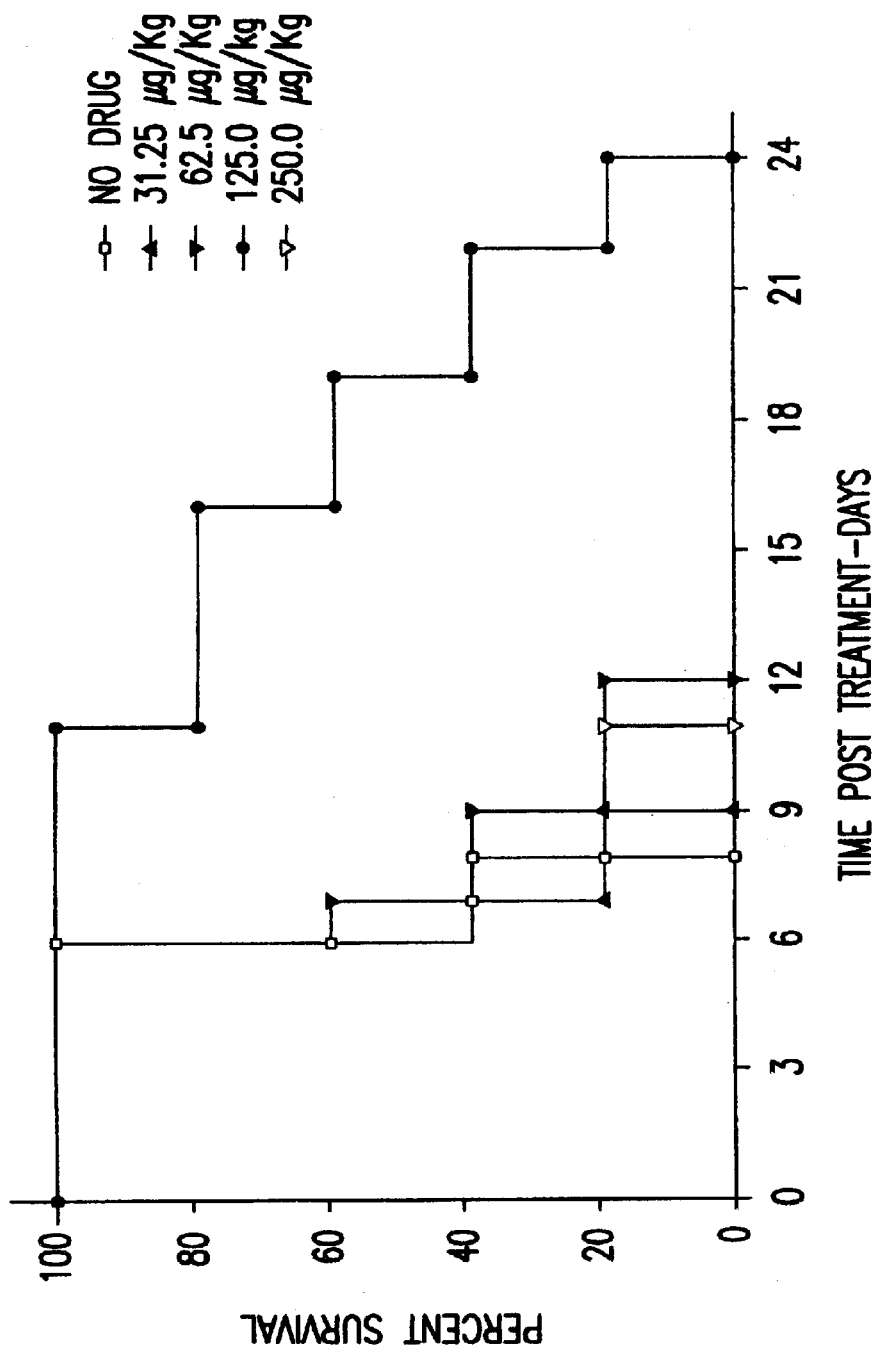
FIG. 3 is an extension of the results in FIG. 2.

The present inventors have conceived of, isolated and applied compounds JO-4 and JO-4A against nucleated infectious agents comprising parasites, bacteria, and the like microorganisms. Fungi and insects likewise are targeted by the instant teachings.

1. General Description and Definitions

The practice of the present invention will employ, unless otherwise indicated, conventional laboratory animal handling techniques, microbiology, parasitology, organic and medicinal chemical synthesis within the skill of the art. Such techniques are explained fully in the literature. See Miller, L. H.; et al., eds; *Immunity to Blood Parasites of Animals and Man*, Plenum Press, New York and London, 1977; Baker, J. R. Muller R, and Rollinson, D. eds., *Advances in Parasitology* Vol.43, Academic Press, 1999; Bogitsh B. J. and Chen T. C. eds. *Human Parasitology* 2nd edition, Academic Press, 1998; Murray, P. R et al. eds; *Medical Microbiology*. Third edition, Mosby, St. Louis, Mo., 1998; Ojo-Amaize, E. A. et al. *Plasmodium berghei* Sporozoites are Mitogenic for Murine T cells, induce Interferon and Activate Natural killer Cells, *J. Immunol.* 1984, 133:1005–1009; Ojo-Amaize, E. A. et al. Positive Correlation between degree of parasitemia, interferon titers, and natural killer cell activity in *Plasmodium Falciparum*-infected Children, *J. Immunol.* 1981, 127:2296–2300; Silverman, R. B; The organic chemistry of Drug Design and Drug Action, Academic Press, Inc. NY (1992); Smith, M. B.; Organic Synthesis, McGraw Hill, Inc. NY, (1994); Okogun, J. I. et al., Z. Naturforsch, 37c:558–561, 1982; Adesomoju, A. A. et al., Phytochemistry 22:2535–236, 1983. Likewise, artisans will understand those conventional techniques used to practice the instant teachings.

The following terminology will be used in accordance with the definitions set out below in describing the present invention.

The term "inhibiting the growth of" is used with respect to protozoan parasites that are pathological to humans or other animals. For example, with respect to protozoan malarial parasites, "inhibiting the growth of" means inhibition of parasitemia as determined by decreased numbers of parasitized red cells in blood which results in alleviating the "pathological effects" of malaria infection and increasing the life span of infected subject.

The term "pathological effects" as used herein is illustrated by an understanding of the life cycle of the protozoan parasite and its effects in a host. It will be understood that protozoans, including those of the genus Plasmodium, Trypanosoma, Theileria, Babesia, Coccidia, Amoebae and the like ciliates (including microsporidians), Trichomonad and related forms, Non-trichomonad flagellates, hemoflagellates (such as Leishmania, Trypanosoma), and other api-complexans such as Bahesia, Toxoplasma, Pneumocystis, Cryptosporidium, Cyclospora and Isospora are described herein. (Bogitsh, B. J. and Cheng, T. C. eds. *Human Para-* sitology 2nd edition, 1998: Academic Press, San Diego, London, Boston, New York etc.).

The protozoan plasmodial parasite causes Malaria, one of the most debilitating diseases afflicting humans and animals. Plasmodia are nucleated Coccidian or Sporozoan parasites of blood cells, and as seen with other coccidia, they require two hosts: the mosquito for the sexual reproductive stages and humans and other animals for the asexual reproductive stages. Human infection is initiated by the bite of an Anopheles mosquito, which introduces infectious plasmodia sporozoites via its saliva into the circulatory system. The sporozoites are carried to the parenchymal cells of the liver where asexual reproduction (schizogony) occurs. This phase of growth is termed the exoerythrocytic cycle and lasts 8–25 days depending on the plasmodial species. The hepatocytes eventually rupture, liberating the plasmodia (termed merozoites at this stage), which in turn attach to specific receptors on the surface of erythrocytes and enter the cells, thus initiating the erythrocytic cycle. Asexual replication progresses through a series of stages (ring, trophozoite, schizont) that culminates in the rupture of the erythrocyte, releasing merozoites, which initiates another cycle of replication by infecting other erythrocytes (Murray, P. R. et al. eds. *Medical MicroBiology* 3rd edition, 1998: Mosby-Year Book, Inc., St. Louis, Mo.).

Pathological and clinical syndromes of malarial parasites consist, in part, of influenza-like symptoms with fever patterns, severe nausea, vomiting and diarrhea, anemia due to destruction of increased numbers of infected erythrocytes resulting in toxic cellular debris, adherence of red blood cells to vascular endothelium and to adjacent red blood cells, and formation of capillary plugging by masses of red blood cells, platelets, leukocytes, and malarial pigment.

It is also known that involvement of the brain (cerebral malaria) is most often seen in *P. falciparum* infection. Capillary plugging from an accumulation of malarial pigment and masses of red cells can result in coma and death. Kidney damage is also associated with *P. falciparum* malaria resulting in an illness called blackwater fever.

Intravascular hemolysis with rapid destruction of red blood cells produces a marked hemoglobinuria and can result in acute renal failure, tubular necrosis, nephrotic syndrome, and death. Liver involvement is characterized by abdominal pain, vomiting of bile, severe diarrhea, and rapid dehydration. Although any malaria infection may be fatal, *P. falciparum* is the most likely to result in death if left untreated. In rodents, *P. berghei*, and *P. chabaudi* infections result in death (Miller, L. H. et al. eds. *Immunity to blood parasites of animals and man*: Advances in Experimental Medicine and Biology, Volume 93, 1977: Plenum Press, New York and London).

As used herein, the term "alleviate" means to mitigate, lessen or reduce or make more bearable. The term "subject" is taken to mean humans as well as other animals.

The following materials and methods were employed in the non-limiting Examples set out below, which illustrate unexpected results noted, those skilled in the art will understand use of the instant teachings with known nucleated infectious agents.

Parasite Strain:
*P. berghei berghei* (E1 Strain Clone B6 of 125674 SF-2393) was purchased from American Type Culture Collection (ATCC), Rockville, Md. The parasites were maintained in vivo and routinely passaged in C57BL/6 strains of mice.

Animals:
Animals used in this work were female C57BL/6 mice, 6–8 wk old, purchased from Charles River Laboratories, Wilmington, Mass.

Parasite Maintenance in vivo:
One vial containing 0.5 ml of *P. berghei*-infected frozen mouse blood, obtained from ATCC, was thawed and injected intraperitoneally (i.p.) into a single mouse. When the mouse was sick, blood was collected by ocular venipuncture into a heparinized tube. Giemsa stained thin blood film smears on glass slides were prepared to determine the level of parasitemia by light microscopy. Infected blood was diluted 1:1000 in HBSS (Hanks Balanced Salt Solution) and 0.3 ml was injected i.p. into a fresh (uninfected) mouse. This process was repeated serially for parasite maintenance in vivo.

Parasite Staining and Diagnosis:
The level of parasitemia was determined by standard technology with thin smears of fresh blood on glass slides, fixed with absolute methanol for 5 minutes, and stained for 30 minutes with 5% Giemsa dye buffered to pH 7.0 to 7.2 (Ojo-Amaize, E. A. et al. J. Immunol. 1981, 127:2296–2300; Murray, P. R. et al. eds. Medical Microbiology. Third edition, Mosby, St. Louis, Mo.; 1998). Stained parasitized red blood cells on glass slides were viewed with 100×1.25 objective lenses in oil immersion under a light microscope (Nikon). At least 1000 red blood cells (RBCs) were counted in each field and 5 fields were counted per slide. The total number of parasitized cells per 1000 RBCs per field was recorded and the average was calculated per slide and expressed in percent (%) of total RBCs.

Treatment of Mice with JO-4A:
For determination of the prophylactic effect of JO-4A on level of blood parasitemia, 5 mice were pretreated p.o. with 1.0 mg/kg once a day for 3 days. Five control mice received vehicle (water) only. On the 4th day after drug pretreatment was stopped, all mice were infected i.p. with 0.1 ml of infected blood diluted 1:100 in HBSS. Blood Samples were obtained from experimental and control mice on days 2,3,4 and 5 post infection to determine the level of blood parasitemia. For determination of mortality, there were 5 groups of 10 mice per group (No drug control, 31.2 $\mu$g/kg, 62.5 $\mu$g/kg, 125.0 $\mu$g/kg and 250 $\mu$g/kg). Experimental mice received appropriate doses of JO-4A p.o. once a day for 4 days prior to infection with *P. berghei* parasites on the 5th day of JO-4A pretreatment. Treatment with JO-4A was continued for 3 more days, once daily, post infection. Mortality of mice was followed daily for 24 days and recorded.

While clinical data and involved mechanisms remain to be further developed it is believed those skilled in the art will readily understand that treatment by the instant compounds and methods for fungal-insect-based, and the like microbiological nucleated agent mediated insult and injury would be routine using any conventional modes of administration, comprising those falling within the scope of the instant claims and such usages and applications would not require undue experimentation to artisans.

Having merely described aspects of the best modes to practice those preferred embodiments which would enable artisans to fully comprehend and practice the teachings of the present invention, it is further noted that various modifications, changes, ameliorations and alterations may be effected by those skilled in the art without impacting on the scope of spirit of the instant invention as defined by the appended claims.

Likewise, the present inventors have used the instant compound to combat related microbiological issues and challenges. For example, it has further been hypothesized that tissues and systems insulted by fungal infestation exhibit with similarly shown improvement under JO-4A treatment.

What is claimed is:

1. A method for treating a subject having a disease caused by infection with a protozoan parasite, the method comprising administering to the subject an effective amount of a compound having the formula:

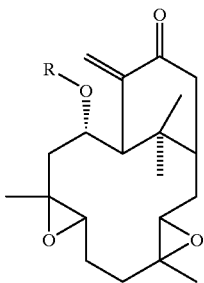

and pharmaceutically acceptable salts thereof, wherein R is selected from the group consisting of
   a) H,
   b) $P(O)(OH)_2$,
   c) $P(O)(OH)(OM)$, wherein M is selected from the group consisting of an alkali metal salt and an alkaline earth metal salt,
   d) $P(O)OM_2$ wherein M is each independently selected from the group consisting of alkali metal salts and alkaline earth metal salts,
   e) Alkyl of 1 to 12 carbon atoms having 0 to 6 double bonds,
   f) $(CH_2)_n$morpholine, wherein n=1–4,
   g) morpholinomethylphenyl, orthoaminophenyl, orthohydroxyphenyl,
   h) $(CH_2)_n COOR_2$, wherein n=1–4, $R_2$ is selected from the group consisting of H, an alkalai metal salt, an alkaline earth metal salt, $NH_4^+$, and $N^+(R_3)_4$, wherein $R_3$ is each independently selected from the group consisting of H and alkyl of 1 to 4 carbon atoms, and
   i) $COR_1$ wherein $R_1$ is selected from the group consisting of H, $(CH_2)_n CH_3$ wherein n=0–6, $(CH_2)_n COOR_2$, wherein n=1–4 and $R_2$ is as previously defined, and $(CH_2)_n N^+(R_3)_4$, wherein n=1–4 and $R_3$ is as previously defined.

2. The method of claim 1, wherein the protozoan parasite belongs to a classification selected from the group consisting of Plasmodian, Trypanosoma, Theileria, Babesia, Amoebae, Trichomonas, Leishmania, Toxoplasma, Pneumocystis, Cryptosporidium, Cyclospora, Isospora, Coccidia, and ciliate, flagellate, and hemoflagellate protozoans.

3. The method of claim 2 wherein the protozoan parasite is selected from the group consisting of *Plasmodium falciparum, Plasmodium vivax, Plasmodium ovale, Plasmodium malariae, Plasmodium berghei, Plasmodium chabaudi, Plasmodium knowlesi, Plasmodium cynomolgi, Plasmodium lophurae* and *Plasmodium yoelii.*

4. The method of claim 1 wherein R is H.

5. The method of claim 4 wherein the disease is malaria.

6. The method of claim 3 wherein R is H.

7. A method for protecting a subject from contracting a disease caused by infection with a protozoan parasite, the method comprising administering to the subject an effective amount of a compound having the formula:

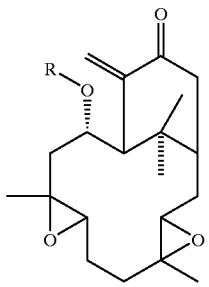

and pharmaceutically acceptable salts thereof, wherein R is selected from the group consisting of
   a) H,
   b) $P(O)(OH)_2$,
   c) $P(O)(OH)(OM)$, wherein M is selected from the group consisting of an alkali metal salt and an alkaline earth metal salt,
   d) $P(O)OM_2$ wherein M is each independently selected from the group consisting of alkali metal salts and alkaline earth metal salts,
   e) Alkyl of 1 to 12 carbon atoms having 0 to 6 double bonds,
   f) $(CH_2)_n$morpholine, wherein n=1–4,
   g) morpholinomethylphenyl, orthoaminophenyl, orthohydroxyphenyl,
   h) $(CH_2)_n COOR_2$, wherein n=1–4, $R_2$ is selected from the group consisting of H, an alkalai metal salt, an alkaline earth metal salt, $NH_4^+$, and $N^+(R_3)_4$, wherein $R_3$ is each independently selected from the group consisting of H and alkyl of 1 to 4 carbon atoms, and
   i) $COR_1$ wherein $R_1$ is selected from the group consisting of H, $(CH_2)_n CH_3$ wherein n=0–6, $(CH_2)_n COOR_2$, wherein n=1–4 and $R_2$ is as previously defined, and $(CH_2)_n N^+(R_3)_4$, wherein n=1–4 and $R_3$ is as previously defined.

8. The method of claim 7, wherein the protozoan parasite belongs to a classification selected from the group consisting of Plasmodian, Trypanosoma, Theileria, Babesia, Amoebae, Trichomonas, Leishmania, Toxoplasma, Pneumocystis, Cryptosporidium, Cyclospora, Isospora, Coccidia, and ciliate, flagellate, and hemoflagellate protozoans.

9. The method of claim 8 wherein the protozoan parasite is selected from the group consisting of *Plasmodium falciparum, Plasmodium vivax, Plasmodium ovale, Plasmodium malariae, Plasmodium berghei, Plasmodium chabaudi, Plasmodium knowlesi, Plasmodium cynomolgi, Plasmodium lophurae* and *Plasmodium yoelii.*

10. The method of claim 7 wherein R is H.

11. The method of claim 10 wherein the disease is malaria.

12. The method of claim 9 wherein R is H.

13. A method for treating a subject having a disease caused by infection with a protozoan parasite, the method comprising administering to the subject an effective amount of a prodrug of a compound having the formula:

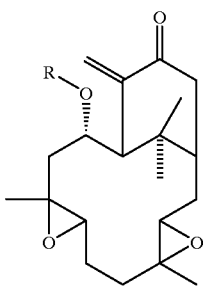

and pharmaceutically acceptable salts thereof, wherein R is selected from the group consisting of
a) H,
b) P(O)(OH)$_2$,
c) P(O)(OH)(OM), wherein M is selected from the group consisting of an alkali metal salt and an alkaline earth metal salt,
d) P(O)OM$_2$ wherein M is each independently selected from the group consisting of alkali metal salts and alkaline earth metal salts,
e) Alkyl of 1 to 12 carbon atoms having 0 to 6 double bonds,
f) (CH$_2$)$_n$morpholine, wherein n=1–4,
g) morpholinomethylphenyl, orthoaminophenyl, orthohydroxyphenyl,
h) (CH$_2$)$_n$COOR$_2$, wherein n=1–4, R$_2$ is selected from the group consisting of H, an alkalai metal salt, an alkaline earth metal salt, NH$_4^+$, and N$^+$(R$_3$)$_4$, wherein R$_3$ is each independently selected from the group consisting of H and alkyl of 1 to 4 carbon atoms, and
i) COR$_1$ wherein R$_1$ is selected from the group consisting of H, (CH$_2$)$_n$CH$_3$ wherein n=0–6, (CH$_2$)$_n$COOR$_2$ wherein n=1–4 and R$_2$ is as previously defined, and (CH$_2$)$_n$N$^+$(R$_3$)$_4$ wherein n=1–4 and R$_3$ is as previously defined.

14. A method for protecting a subject from contracting a disease caused by infection with a protozoan parasite, the method comprising administering to the subject an effective amount of a prodrug of a compound having the formula:

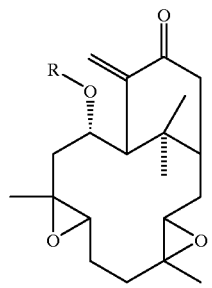

and pharmaceutically acceptable salts thereof, wherein R is selected from the group consisting of
a) H,
b) P(O)(OH)$_2$,
c) P(O)(OH)(OM), wherein M is selected from the group consisting of an alkali metal salt and an alkaline earth metal salt,
d) P(O)OM$_2$ wherein M is each independently selected from the group consisting of alkali metal salts and alkaline earth metal salts,
e) Alkyl of 1 to 12 carbon atoms having 0 to 6 double bonds,
f) (CH$_2$)$_n$morpholine, wherein n=1–4,
g) morpholinomethylphenyl, orthoaminophenyl, orthohydroxyphenyl,
h) (CH$_2$)$_n$COOR$_2$ wherein n=1–4 and R$_2$ is selected from the group consisting of H, an alkalai metal salt, an alkaline earth metal salt, NH$_4^+$, and N$^+$(R$_3$)$_4$, wherein R$_3$ is each independently selected from the group consisting of H and alkyl of 1 to 4 carbon atoms, and
i) COR$_1$ wherein R$_1$ is selected from the group consisting of H, (CH$_2$)$_n$CH$_3$ wherein n=0–6,(CH$_2$)$_n$COOR$_2$ wherein n=1–4 and R$_2$ is as previously defined, and (CH$_2$)$_n$N$^+$(R$_3$)$_4$ wherein n=1–4 and R$_3$ is as previously defined.

* * * * *